United States Patent
Yang et al.

(10) Patent No.: US 6,413,223 B1
(45) Date of Patent: Jul. 2, 2002

(54) CUFFLESS CONTINUOUS BLOOD PRESSURE MONITOR

(75) Inventors: Boo-Ho Yang, Boston; Yi Zhang, Cambridge; Haruhiko H. Asada, Lincoln, all of MA (US)

(73) Assignee: Massachussetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/585,382

(22) Filed: Jun. 1, 2000

Related U.S. Application Data

(60) Provisional application No. 60/137,033, filed on Jun. 1, 1999.

(51) Int. Cl.$^7$ ................................................. A61B 5/02
(52) U.S. Cl. ...................................... 600/485; 600/500
(58) Field of Search ................................. 600/485, 500

(56) References Cited

U.S. PATENT DOCUMENTS

| | | | |
|---|---|---|---|
| 5,833,618 A | 11/1998 | Caro et al. ................... | 600/485 |
| 5,964,701 A | * 10/1999 | Asada et al. ................ | 600/300 |

OTHER PUBLICATIONS

Pressman et al. "A Transducer for the Continuous External Measurement of Arterial Blood Pressure" IEEE Transactions on Bio–Medical Electronics 10:73–81 (1961).

Yamakoshi et al. "Indirect Measurement of Instantaneous Arterial Blood Pressure in the Human Finger by the Vascular Unloading Technique" IEEE Transactions on Bio–Medical Electronics 27:150–155 (1980).

Clark, Jr. et al. "A Two–Stage Identification Scheme for the Determination of the Parameters of a Model of the Left Heart and Systemic Circulation" IEEE Transactions on Bio–Medical Electronics 27:20–29 (1980).

Stettler et al. "Theoretical Analysis of Arterial Hemodynamics Including the Influence of Bifurcations" Annals of Biomedical Engineering 9:145–164 (1981).

Clark "Extracting New Information from the Shape of the Blood Pressure Pulse" Master's Thesis 1–117 Massachusetts Institute of Technology (1990).

Kawarada et al. "Ambulatory Monitoring of Indirect Beat–To–Beat Arterial Pressure in Human Fingers by a Volume–Compensation Method" Medical & Biological Engineering & Computing 34:55–62 (1991).

(List continued on next page.)

*Primary Examiner*—Robert L. Nasser
*Assistant Examiner*—Patricia Mallari
(74) *Attorney, Agent, or Firm*—Bromberg & Sunstein LLP

(57) ABSTRACT

A device for noninvasive, continuous monitoring of arterial blood pressure for advanced cardiovascular diagnoses. Most of the current noninvasive, continuous blood pressure measurement devices are mechanically intrusive and, therefore, cannot be used for long-term ambulatory monitoring. This new approach requires only simple, noninvasive monitoring devices such as finger photoplethysmographs and an electrical impedance photoplethysmograph (EIP) to monitor the dynamic behavior of the arterial blood flow. In this approach, measured signals from these noninvasive sensors on an arterial segment are integrated to estimate the blood pressure in the segment based on a hemodynamic model. A mathematical model of the arterial blood flow is derived and transformed into a state-space representation. In the modeling, a precise hemodynamic model for the arterial segment on which sensors are located is derived, and combined with relatively simplified models of the upstream and the downstream arterial flows to represent an entire arterial stream. Then, a Kalman filter is designed based on the model and it is shown that the internal variables such as the arterial blood pressure in the arterial segment can be estimated based on the measurements, even though the observability condition of the system may not be met. Simulation results indicate that the approach can generate an accurate estimation of the arterial blood pressure in real-time even from noisy sensor signals.

9 Claims, 6 Drawing Sheets

OTHER PUBLICATIONS

Johnson et al. "A Model of Pulsatile Flow in a Uniform Deformable Vessel" Journal of Biomechanics 25:91–100 (1992).

Welkowitz et al. "Noninvasive Estimation of Cardiac Output" IEEE Transactions on Biomedical Engineering 38(11):1100–1105 (1991).

Grewal et al. "Linear Optimal Filters, Predictors and Smoothers" Kalman Filtering Theory and Practice 108–116 (1993).

Ozawa "A Numerical Model of the Cardiovascular System of Clinical Assessment of the Hemodynamic State" Ph.D. Thesis Department of Health Sciences and Technology Massachusetts Institute of Technology (1996).

Guarini et al. "Estimation of Cardia Function from Computer Analysis of the Arterial Pressure Waveform" IEEE Transactions of Biomedical Engineering 45(12):1420–1428 (1998).

Leslie, et al. "Digital artery diameters: An anatomic and clinical study" Journal of Hand Surgery, vol. 12A, No. 5, Part 1740–743 (1987).

Belardinelli et al. "A New Nonlinear Two–Dimensional Model of Blood Motion in Tapered and Elastic Vessels" Computers in Biology and Medicine, vol. 21 1–13 (1991).

Belardinelli et al. "Theoretical Analysis of Pressure Pulse Propagation in Arterial Vessels" Journal of Biomechanics, vol. 25 1337–1349 (1992).

Penaz "Photoelectric Measurement of Blood Pressure, Volume and Flow in the Finger" Digest of the 10th International Conference on Medical and Biological Engineering (1973).

Spector "Handbook of Biological Data" W.B. Saunders Company, Philadelphia (1956).

Kailath "Algebraic Controllability Theorem" Linear Systems Prentice–Hall, NJ (1980).

Li "Aterial System Dynamics" New York University Press, New York (1987).

European Patent Office PCT International Search Report PCT/US00/15006 Aug. 22, 2000.

European Patent Office PCT Partial International Search Report–Invitation To Pay/Add Fees PCT/US00/10429 Aug. 24, 2000.

International Preliminary Examination for PCT/US00/150061, Sep. 26, 2001.

Finapres (FINger Arterial PRESsure), Biomedical Instrumentation, *http://www.bmi–tno.nl/about/expertise finapres en.htm*.

Portapres, Biomedical Instrumentation, *http://www.bmi–tno.nl/products/portapres_en.htm*.

Abstract for Finger Arterial Pressure with Finapres, Zeitschrift fur Kardiologie, 85 Suppl 3:38–44, 1996, *http://www.bmi–tno.nl/scripts/reference.cgi?id=30*.

Abstract for Reconstruction of Brachial Artery Pressure from Noninvasive Finger Pressure Measurements, Circulation, 94(8):1870–5, Oct. 15, 1996, *http://www.bmi–tno.nl/scripts/reference.cgi?id=2*.

* cited by examiner

CUFFLESS CONTINUOUS BLOOD PRESSURE MONITOR

PRIORITY

This application claims priority from U.S. provisional application serial No. 60/137,033 filed Jun. 1, 1999, entitled "Cuffless Continuous Blood Pressure Monitor" which is incorporated herein, by reference.

TECHNICAL FIELD

The present invention relates to a device and method for monitoring the blood pressure of a patient and, more particularly, for deriving the blood pressure from measurements performed continuously on the finger of the patient.

BACKGROUND OF THE INVENTION

Noninvasive ambulatory blood pressure monitoring is currently limited to the simple measurements of systolic and diastolic blood pressures at intervals. However, it is known to clinicians that continuous waveforms of the blood pressure can provide more useful information about the patient's cardiovascular state that are difficult to obtain from the routine antecubital pressure measurement. For example, the rate of pressure rise at the beginning of systole indicates the strength of cardiac contraction while the rate of pressure decay during end diastole can be used as a measure of peripheral vascular resistance, both of which are important parameters used in cardiovascular diagnoses. In fact, many numerical algorithms have been developed to estimate left-ventricular and circulatory parameters from the arterial pressure waveform by applying a computer model of the cardiovascular system, as described by J. W. Clark, et al., "A Two-Stage Identification Scheme for the Determination of the Parameters of a Model of the Left Heart and Systemic Circulation," IEEE Trans. on Biomed. Eng., Vol. 27, pp. 20–29, January, 1980; W. Welkowitz, Q. Cui, Y. Qi and J. Kostis, "Noninvasive Estimation of Cardiac Output," IEEE Trans. on Biomed. Eng., Vol. 38, pp. 1100–1105, November, 1991; M. Guarini, J. Urzua, A. Cipriano, and W. Gonzalez, "Estimation of Cardiac Function From Computer Analysis of the Arterial Pressure Waveform," IEEE Trans. on Biomed. Eng., Vol. 45, pp. 1420–1428, December 1998; and E. T. Ozawa, "A Numerical Model of the Cardiovascular System for Clinical Assessment of the Hemodynamic State," Ph.D. Thesis, Dept. of Health Sciences and Technology, MIT, September, 1996. Considering that heart disease is a prevalent cause of death in the modern society, it is obvious that long-term noninvasive continuous monitoring of such pressure waveforms would bring enormous improvement of the quality of healthcare at home as well as in the hospital.

A few devices have been developed for continuous monitoring of the arterial pressure waveform, yet these are either invasive or mechanically intrusive and are not designed for the long-term use. For example, Pressman and Newgard developed a noninvasive method for continuously measuring the instantaneous blood pressure by applying the coplanar measurement principle used by tonometry, as described in G. Pressman and P. Newgard, "A Transducer for Continuous External Measurement of Arterial Blood Pressure," IEEE Trans. on Biomed. Eng., Vol. 10, pp. 73–81, 1961. In this method, called "arterial tonometry," the artery is flattened by applying external pressure non-invasively to squeeze the artery against the bone. Since the circumferential tension of the arterial wall disappears, the applied pressure to maintain the flattened shape indicates the arterial blood pressure. An array of piezoelectric transducers is used for the pressure reading. Penaz, on the other hand, proposed a new noninvasive, continuous blood pressure measuring method based on the principle of vascular wall unloading, as described in Penaz, "Photo-electric Measurement of Blood Pressure, Volume and Flow in the Finger," Digest of the 10-th Int. Conf. on Medical and Biolog. Eng., 1973. In this method, a cuff is inflated to a pressure equal to the pressure in the artery and the cuff pressure is continuously adjusted by a servo control system, which monitors the size of the artery using a photoplethysmograph. This method was further developed by Wesseling, as described in K. H. Wesseling, "Non-invasive, Continuous, Calibrated Blood Pressure by the Method of Penaz," Blood Pressure Measurement and Systemic Hypertension, pp.163–175, Medical World Press, and successfully commercialized as "FINAPRES." Yamakoshi and his group also developed a similar device independently by applying the vascular unloading technique, as described in C. Tase and A. Okuaki, "Noninvasive Continuous Blood Pressure Measurement—Clinical Application of FINAPRES—," Japanese J. of Clinical Monitor, Vol. 1, pp. 61–68, 1990; and K. Yamakoshi, H. Shimazu, and T. Togawa, "Indirect Measurement of Instantaneous Arterial Blood Pressure in the Human Finger by the Vascular Unloading Technique," IEEE Trans. on Biomed. Eng., Vol. 27, pp. 150–155, 1980. The major drawback of these devices, however, is the tight confinement and mechanical intrusiveness of the sensor probes and the resultant discomfort to the patient. As stated above, these methods require a constant and continuous external pressure on the skin surface of the patient and it could cause vasospasm and pressure drops in the peripheral artery, as described in A. Kawarada, H. Shimazu, H. Ito, and K. Yamakoshi, "Ambulatory Monitoring of Indirect Beat-to-Beat Arterial Pressure in Human Fingers by a Volume-Compensation Method," Med Biol Eng Comput, Vol. 34, pp. 55–62, January 1991. For long-term, ambulatory blood pressure monitoring, a new method for the noninvasive and non-intrusive continuous measurement is preferable.

SUMMARY OF THE INVENTION

In accordance with one aspect of the invention, a system for monitoring a blood pressure of a patient uses a first photoplethysmograph proximate to a finger of the patient for providing a measure of change in the arterial diameter at a first location of a specified artery of the patient. A second photoplethysmograph proximate to the finger of the patient and displaced relative to the first photoplethysmograph provides a measure of change in the arterial diameter at a second location of the specified artery of the patient. An electrical impedance plethysmograph in electrical contact with the finger of the patient provides a measure of change in the electrical impedance of an arterial segment between the first and the second locations of the specified artery. A controller derives a measure of the blood pressure of the patient based on the measures of change in the arterial diameter at the first and second locations of the specified artery and the measure of change in the electrical impedance of an arterial segment.

In a further related embodiment, the first photoplethysmograph is borne by the patient on a finger ring. In another related embodiment, the first photoplethysmograph is borne by the patient on a first band of a finger ring and the second photoplethysmograph is borne by the patient on a second band of the finger ring. In some embodiments, a transmitter may optionally be used for transmitting the measure of the blood pressure of the patient to a remote location.

In another embodiment, a system for monitoring a blood pressure of a patient uses a monitor having a first and a second band to be worn by the patient on a single finger. The monitor has a first photoplethysmograph disposed on the first band for providing a first signal based on a first arterial diameter of the patient, a second photoplethysmograph disposed on the second band for providing a second signal based on a second arterial diameter of the patient, and an electrical impedance plethysmograph disposed on the first and second bands for providing a third signal based on the electrical impedance of the a segment of an artery of the patient. A controller analyzes the first, second, and third signals and determines a measure of the blood pressure of the patient.

In accordance with another embodiment, a method for monitoring the blood pressure of a patient derives a measure of change in both the diameter of the first and second end of a segment of an artery of the patient. A model of arterial blood flow is applied to the derived measures of change in the diameters of the first and second ends of the arterial segment and the volume of the segment for calculating the instantaneous blood pressure of the patient. In a related embodiment, the step of deriving the measure of change in the diameter of the first end of a segment of an artery includes receiving a signal of a first photoplethysmograph. In another related embodiment, the step of deriving the measure of change in the diameter of the second end of a segment of an artery includes receiving a signal of a second photoplethysmograph. In some embodiments, a Kalman filter is used for estimating internal state variables.

BRIEF DESCRIPTION OF THE DRAWINGS

The foregoing features of the invention will be more readily understood by reference to the following detailed description, taken with reference to the accompanying drawings, in which.

DESCRIPTION OF SPECIFIC EMBODIMENTS

A new approach to noninvasive non-intrusive continuous measurement of pulsating arterial blood pressure is now described which does not require the use of a cuff. In accordance with embodiments of the invention, information gathered by multiple sources and sensors are merged to provide improved insight into the phenomena under consideration. The use of sensor fusion is applied for indirectly estimating arterial blood pressure by integrating simultaneous measurements from noninvasive, non-intrusive sensors such as a photoplethysmograph and a bioelectrical impedance plethysmograph with a mathematical model of the blood flow.

The present invention may be applied in the context of finger-sensors such as those described in U.S. Pat. No. 5,964,701 which is herein incorporated by reference.

Figure 1:
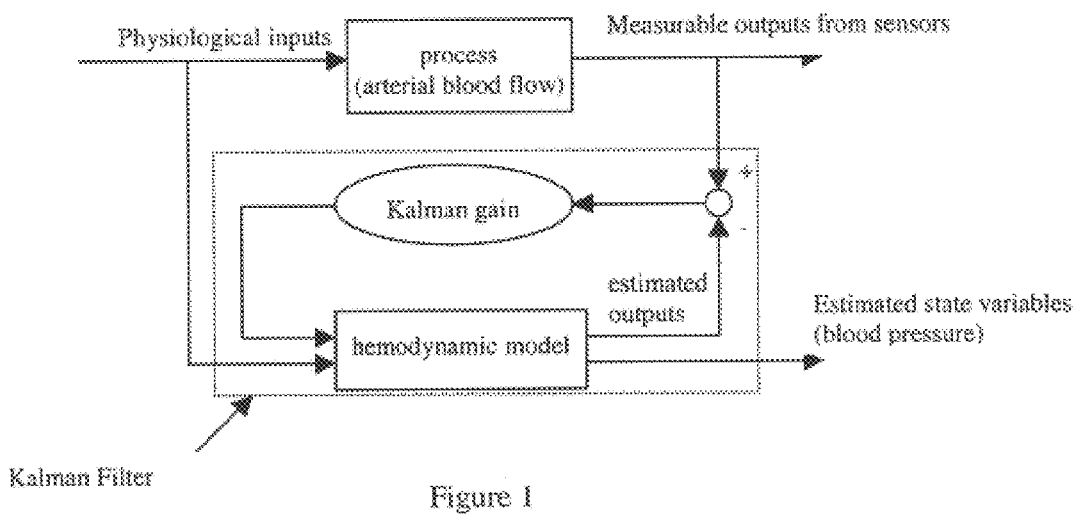
FIG. 1 schematically shows a Kalman filter for instantaneous blood pressure estimation in accordance with an embodiment of the present invention.

In this approach, a Kalman filter is used for the sensor fusion scheme. Kalman filters are the standard state estimators or observers that are optimum with respect to the process noise and sensor noise, and many nonlinear extensions have been developed, and are well known to people skilled in the art, as described in R. G. Brown and P. Y. Z. Hwang, Introduction to Random Signals and Applied Kalman Filtering, John Wiley and Son, 1997, hereby incorporated by reference. In accordance with preferred embodiments, a state-space equation is derived from a mathematical hemodynamic model and a Kalman filter is applied to estimate the internal state variables such as the blood pressure based on signals from noninvasive and non-intrusive sensors. FIG. 1 shows the basic scheme of this approach.

Furthermore, in accordance with preferred embodiments, a two-dimensional mathematical model of the arterial blood flow is derived as an incompressible, axially symmetric Newtonian fluid in a rectilinear, viscoelastic thick shell of isotropic, incompressible material with a circular section. The modeling method is applied to a small digital arterial segment, from which sensor signals such as a photoplethysmograph and a bioelectrical impedance plethysmograph are obtained. Then, the hemodynamic model of the peripheral arterial segment is extended up to the heart as the proximal boundary and the capillary as the distal boundary to represent an entire arterial stream. A commonly assumed pattern of the cardiac output is used as the system's input. To avoid high-order modeling, the upstream is modeled as a three-dimensional Windkessel model, and the downstream is modeled as simple impedance. Finally, a Kalman filter is designed based on the extended model. Since the original local arterial segment are precisely modeled and the output signals are measured from the segment, it is expected that the Kalman filter can estimate the local arterial blood pressure accurately even with the simplifications of the input and the modeling of the upstream and downstream blood flows.

State-Space Modeling of Arterial Hemodynamics

A mathematical hemodynamic model is used for the complex behavior of the arterial vessel and blood flow of a peripheral arterial segment and internal variables such as the blood pressure are estimated by comparing the sensor readings from the segment with the simulated outputs. Therefore, the accuracy and fidelity of the local model is a key issue. Many hemodynamic models have been developed for the study of the two-dimensional nonlinear behavior of the pulsating blood flow, as described in J. C. Stettler, P. Niederer and M. Anliker, "Theoretical Analysis of Arterial Hemodynamics including the Influence of Bifurcations," Annals of Biomed. Eng., Vol. 9, pp. 145–164, 1981; and G. A. Johnson, H. S. Borovetz, and J. L. Anderson, "A Model of Pulsatile Flow in a Uniform Deformable Vessel," J. of Biomechanics, Vol. 25, pp. 91–100, 1992. A mathematical framework developed by Belardinelli and Cavalcanti, as described in E. Belardinelli and S. Cavalcanti, "A New Nonlinear Two-Dimensional Model of Blood Motion in Tapered and Elastic Vessels," Comput. Biol. Med., Vol. 21, pp. 1–13, 1991; and E. Belardinelli and S. Cavalcanti, "Theoretical Analysis of Pressure Pulse Propagation in Arterial 35 Vessels," J. of Biomechanics, Vol. 25, pp. 1337–1349, 1992, is applied which describes a two-dimensional nonlinear flow of Newtonian viscous fluid moving in a deformable tapered tube. The papers of Belardinelli and Cavalcanti are appended hereto and incorporated herein by reference. The upstream and the downstream arterial flows are represented as an extended Windkessel model, and combined with the above nonlinear model of the local segment to constitute the entire arterial stream.

Local Arterial Flow Model

Mathematical Model of Arterial Flow

Figure 2:
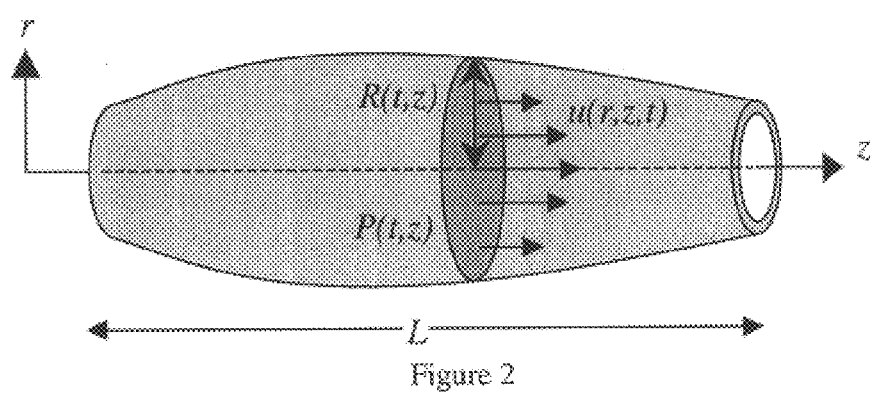
FIG. 2 shows a segment of a viscoelastic artery with length of L.

A small segment (distance of L) of a small artery such as a digital artery is shown in FIG. 2. The arterial vessel is assumed to be a rectilinear, deformable, thick shell of isotropic, incompressible material with a circular section and without longitudinal movements. Blood is an incompressible Newtonian fluid and flow is axially symmetric. Two-dimensional Navier-Stokes equations and continuity equation for a Newtonian and incompressible fluid in cylindrical coordinate $(r, \theta, z)$ are:

$$\frac{\partial u}{\partial t} + w\frac{\partial u}{\partial r} + u\frac{\partial u}{\partial z} = -\frac{1}{\rho}\frac{\partial P}{\partial z} + \nu\left(\frac{\partial^2 u}{\partial r^2} + \frac{1}{r}\frac{\partial u}{\partial r} + \frac{\partial^2 u}{\partial z^2}\right) \quad (1)$$

$$\frac{\partial w}{\partial t} + w\frac{\partial w}{\partial r} + u\frac{\partial w}{\partial z} = -\frac{1}{\rho}\frac{\partial P}{\partial r} + \nu\left(\frac{\partial^2 w}{\partial r^2} + \frac{1}{r}\frac{\partial w}{\partial r} + \frac{\partial^2 w}{\partial z^2} - \frac{w}{r^2}\right) \quad (2)$$

$$\frac{1}{r}\frac{\partial}{\partial r}(rw) + \frac{\partial u}{\partial z} = 0 \quad (3)$$

where P denotes pressure, $\rho$ density, $\nu$ kinematic viscosity, and $u=u(r,z,t)$ and $w=w(r,z,t)$ denote the components of velocity in axial (z) and radial (r) directions respectively, as shown in FIG. 2. Let $R(z,t)$ denote the inner radius of the vessel and define a new variable:

$$\eta = \frac{r}{R(z, t)} \quad (4)$$

The pressure P is assumed to be uniform within the cross section so that P is independent of the radial coordinate, $\eta$, i.e. $P=P(z,t)$. The above equations can be rewritten in a new coordinate $(\eta, \theta, z)$ as $$\frac{\partial u}{\partial t} - \frac{1}{R}\left(\eta\left(u\frac{\partial R}{\partial z} + \frac{\partial R}{\partial t}\right) - w\right)\frac{\partial u}{\partial \eta} + u\frac{\partial u}{\partial z} = -\frac{1}{\rho}\frac{\partial P}{\partial z} + \frac{\nu}{R^2}\left(\frac{\partial^2 u}{\partial \eta^2} + \frac{1}{\eta}\frac{\partial u}{\partial \eta}\right) \quad (5)$$

$$\frac{\partial w}{\partial t} + \frac{1}{R}\left(\eta\left(u\frac{\partial R}{\partial z} + \frac{\partial R}{\partial t}\right) - w\right)\frac{\partial w}{\partial \eta} + u\frac{\partial w}{\partial z} = \frac{\nu}{R^2}\left(\frac{\partial^2 w}{\partial \eta^2} + \frac{1}{\eta}\frac{\partial w}{\partial \eta} - \frac{w}{\eta^2}\right) \quad (6)$$

$$\frac{1}{R}\frac{\partial w}{\partial \eta} + \frac{w}{\eta R} + \frac{\partial u}{\partial z} - \frac{\eta}{R}\frac{\partial R}{\partial z}\frac{\partial u}{\partial \eta} = 0 \quad (7)$$

where it can be assumed:

$$\frac{\partial^2 u}{\partial z^2} \ll 1, \quad \frac{\partial^2 w}{\partial z^2} \ll 1, \quad \frac{\partial P}{\partial r} \ll 1$$

The boundary conditions for the above equations in $\eta$ axis are:

$$w(\eta, z, t)|_{\eta=0} = 0, \quad w(\eta, z, t)|_{\eta=1} = \frac{\partial R}{\partial t}, \quad (8)$$

$$u(\eta, z, t)|_{\eta=1} = 0, \quad \left.\frac{\partial u}{\partial \eta}\right|_{\eta=0} = 0$$

The basic idea of this hemodynamic modeling, described by E. Belardinelli and S. Cavalcanti, is to assume that the velocity profile in the axial direction can be expressed as the following polynomial form:

$$u(\eta, z, t) = \sum_{k=1}^{N} q_k(\eta^{2k} - 1) \quad (9)$$

The velocity profile in the radial direction is also expressed as:

$$w(\eta, z, t) = \frac{\partial R}{\partial z}\eta w + \frac{\partial R}{\partial t}\eta - \frac{\partial R}{\partial t}\frac{1}{N}\eta\sum_{k=1}^{N}\frac{1}{k}(\eta^{2k} - 1) \quad (10)$$

For simplicity, N=1, such as $$u(\eta, z, t) = q(z, t)(\eta^2 - 1) \quad (11)$$

$$w(\eta, z, t) = \frac{\partial R}{\partial z}\eta w + \frac{\partial R}{\partial t}\eta - \frac{\partial R}{\partial t}\eta(\eta^2 - 1) \quad (12)$$

By plugging eqs.(11) and (12) into eqs.(5) and (7), the dynamic equations of $q(z,t)$ and $R(z,t)$ are obtained as:

$$\frac{\partial q}{\partial t} - \frac{4q}{R}\frac{\partial R}{\partial t} - \frac{2q^2}{R}\frac{\partial R}{\partial z} + \frac{4\nu}{R^2}q + \frac{1}{\rho}\frac{\partial P}{\partial z} = 0 \quad (13)$$

$$2R\frac{\partial R}{\partial t} + \frac{R^2}{2}\frac{\partial q}{\partial z} + q\frac{\partial R}{\partial z} = 0 \quad (14)$$

Complete derivations of the above equations are described by described by E. Belardinelli and S. Cavalcanti. The cross-sectional area $S(z,t)$ and blood flow $Q(z,t)$ can be defined as:

$$S = \pi R^2, \quad Q = \int\int_S u\, d\eta = \frac{1}{2}\pi q R^2$$

Then, eqs.(13) and (14) can be re-written in terms of Q and S as:

$$\frac{\partial Q}{\partial t} - \frac{3Q}{S}\frac{\partial S}{\partial t} - \frac{2Q^2}{S^2}\frac{\partial S}{\partial z} + \frac{4\pi v}{S}Q + \frac{S}{2\rho}\frac{\partial P}{\partial z} = 0 \quad (15)$$

$$\frac{\partial S}{\partial t} + \frac{\partial Q}{\partial z} = 0 \quad (16)$$

Viscoelastic Model of Arterial Wall

Figure 3:
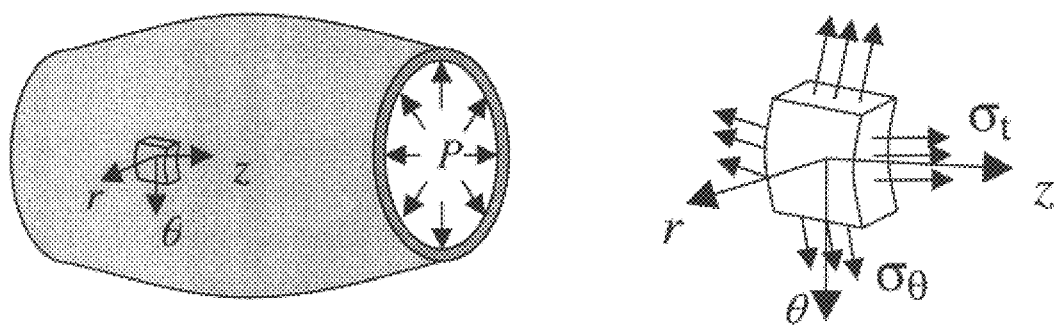
FIG. 3 shows a state of stress in a thin-walled, viscoelastic blood vessel.

To understand the hemodynamics of arterial blood flow, a modeling of the viscoelastic behavior of the arterial wall is essential. A constitutive law of the arterial wall is derived from the stress-strain relationship of the material w. Let $\sigma_\theta$ and $\sigma_t$ be the circumferential stress and tangential stress respectively as shown in FIG. 3. Ignoring the inertia of the arterial wall and the external pressure, equilibrium with the blood pressure gives:

$$PR = \sigma_\theta e - \sigma_t e R \frac{\partial^2 R}{\partial z^2} \quad (17)$$

where R(z t) and e are the radius of the arterial vessel and the thickness of the arterial wall respectively.

From the geometric compatibility of the blood vessel, an expression of strains can be obtained such as $$\varepsilon_\theta = \frac{R - R_0}{R_0}, \varepsilon_t = \sqrt{1 + \left(\frac{\partial R}{\partial z}\right)^2} - 1 \quad (18)$$

where $\epsilon_\theta$ and $\epsilon_t$ are circumferential and tangential strains respectively and a constant $R_0$ is the radius of the artery when P(z,t)=0 and the system is in a steady state.

The most widely used model to describe the viscoelastic properties of the arterial wall is the Kelvin-Voigt model, in which the stress-strain relationship is described as:

$$\sigma_\theta = E\varepsilon_\theta + \eta\frac{\partial \varepsilon_\theta}{\partial t}, \sigma_t = E\varepsilon_t + \eta\frac{\partial \varepsilon_t}{\partial t} \quad (19)$$

in which E is the elastic modulus and $\eta$ is the damping coefficient. By plugging eqs.(18) and (19) with $S_0=\pi R_0^2$ and eliminating second and higher order terms, the following equation is obtained describing the viscoelastic constitutive law of the arterial wall:

$$P = \frac{\sqrt{\pi} Ee}{S\sqrt{S_0}}\left(S + \frac{\eta}{2E}\frac{\partial S}{\partial t} - \sqrt{S_0 S}\right) \quad (20)$$

Discretization

The above nonlinear, partial differential equations given in eqs.(15), (16) and (20) are discretized and transformed into a state equation using a finite-difference method. First, the segment of the artery (length L) is equally divided by N grids with a step size of $\Delta z=L/(N-1)$. The mesh points in the finite difference grids are represented by j where j=1,2, . . . ,N and N>2. If the length of the arterial element $\Delta z$ is sufficiently small then it is possible to approximate—in each section—the derivatives with respect to the axial coordinate z with the following finite difference scheme:

$$\frac{\partial S_i}{\partial z} = \frac{S_{i+1} - S_i}{\Delta z}, \frac{\partial P_i}{\partial z} = \frac{P_{i+1} - P_i}{\Delta z}, \frac{\partial Q_i}{\partial z} = \frac{Q_i - Q_{i-1}}{\Delta z} \quad (21)$$

Figure 4:
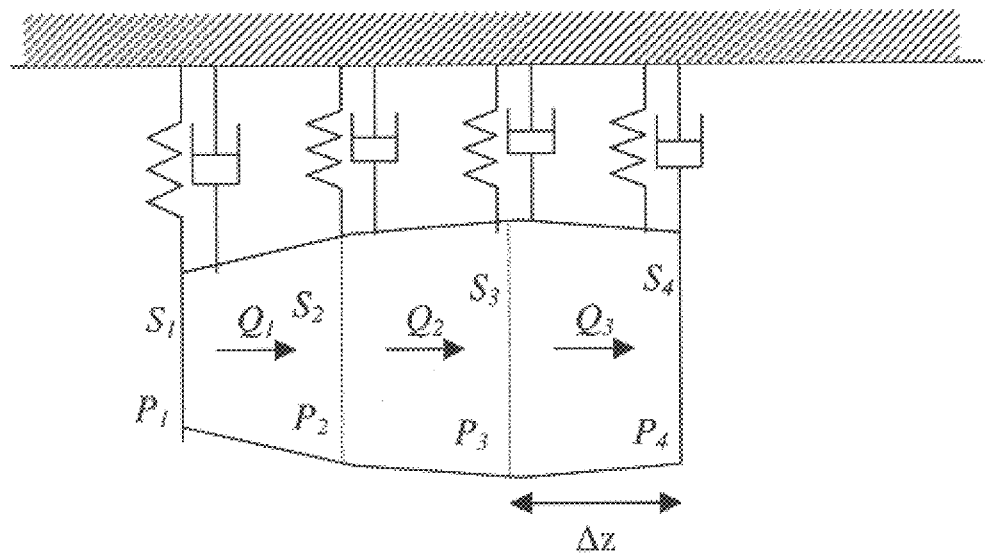
FIG. 4 shows discretization of the hemodynamic model of a digital arterial segment.

The constitutive law given in eq. (20) is modeled such that the viscoelasticity applies only at mesh points. An example of the discretization when N=4 is shown in FIG. 4. Using the above equations, the hemodynamic model given in eqs.(15) and (16) can be discretized as $$\frac{dQ_i}{dt} + \frac{3Q_i}{S_i}\frac{Q_i - Q_{i-1}}{\Delta z} - \frac{2Q_i^2}{S_i^2}\frac{S_{i+1} - S_i}{\Delta z} + \frac{4\pi v}{S_i}Q_i + \frac{S_i}{2\rho}\frac{P_{i+1} - P_i}{\Delta z} = 0 \quad (22)$$

$$\frac{dS_i}{dt} = -\frac{Q_i - Q_{i-1}}{\Delta z} \quad (23)$$

To complete the discretization of the hemodynamic model, the boundary condition at proximal ($P_1$, $Q_0$) and distal ($P_N$, $Q_N$) extremities of the arterial segment must be defined appropriately.

Upstream Blood Flow

Upstream dynamics extends the proximal boundary ($P_1$, $Q_0$) up to the heart so that the commonly assumed pattern of the cardiac output can be used as the input to the system. For simplicity, a lumped model is used to describe the upstream dynamics. A large amount of work has been done in this area. In accordance with a preferred embodiment, a four-element modified Windkessel model is applied, as described in G. Landes. Einige untersuchungen an elektrischen analogie-schaltungen zum kreislauf-system. Z. Biol., 101:410, (1943) This model has been adopted by many researchers for the arterial pressure waveform analysis, as described in K. P Clark.Extracting new information from the shape of the blood pressure pulse. Master's thesis, Massachusetts Institute of Technology, Cambridge, Mass., 1991.

Figure 5:
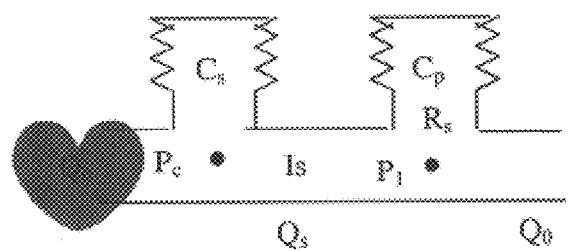
FIG. 5 shows an extended Windkessel model for upstream dynamics.

FIG. 5 shows the modified Windkessel model. The aorta and major arteries are modeled as a single elastic chamber ($C_s$) which stores the blood ejected from the left ventricle during a systole. The distal vessels are modeled as capacitive ($C_p$) and resistive ($R_s$) elements through which the blood drains during a diastole. The oscillatory effect of blood propagation is taken into account by introducing an effective mass ($I_s$). The dynamic equation for the upstream is derived as below, where $Q_c$ is the cardiac output:

$$\frac{dP_c}{dt} = \frac{1}{C_s}(Q_c - Q_s) \quad (24)$$

$$\frac{dQ_s}{dt} = \frac{1}{I_s}(P_c - P_1) \quad (25)$$

$$\frac{dP_1}{dt} = \frac{1}{C_p}\left(Q_s - Q_0 - \frac{P_1}{R_s}\right) \quad (26)$$

where $Q_0$ can be solved from the constitutive law of the arterial wall on the $1^{st}$ node of the local model derived in the previous section:

$$P_1 = \frac{\sqrt{\pi} Ee}{S_1\sqrt{S_0}}\left(S_1 - \frac{\eta}{2E}\frac{Q_1 - Q_0}{\Delta Z} - \sqrt{S_0 S_1}\right) \quad (27)$$

Downstream Blood Flow

Figure 6:
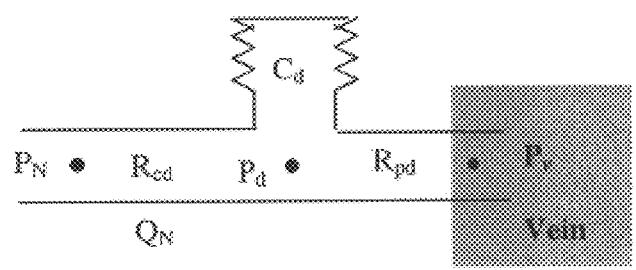
FIG. 6 shows a classic Windkessel model for downstream dynamics.

Similarly, the downstream dynamics extends the distal boundary ($P_N$, $Q_N$) to the end of arteries. Veins can be easily modeled as a reservoir when concerned with arterial hemodynamics. Since digital arteries are being monitored, which is close to veins, the inertia term in the downstream is negligible. The classic Windkessel model is used to model the downstream as shown in FIG. 6, where $C_d$ is the compliance of the vessels in downstream, $R_{cd}$ is the characteristic resistance, $R_{pd}$ is the peripheral resistance, $P_v$ is an effort source if no interest in venous dynamics.

The dynamic equation for the downstream can be written as:

$$\frac{dP_d}{dt} = \frac{1}{C_d}\left(Q_N - \frac{P_d - P_v}{R_{pd}}\right) \quad (28)$$

Where $Q_N$ can be solved from the algebraic equation and the constitutive law of the arterial wall on the $N^{th}$ node:

$$Q_N = \frac{P_N - P_d}{R_{cd}}, \quad (29)$$

$$P_N = \frac{\sqrt{\pi}\,Ee}{S_N \sqrt{S_0}}\left(S_N - \frac{\eta}{2E}\frac{Q_N - Q_{N-1}}{\Delta Z} - \sqrt{S_0 S_N}\right)$$

Entire Arterial Model

In this section, the models for the local arterial hemodynamics and the upstream/downstream dynamics, described above, are integrated to represent an entire systematic arterial stream.

The entire arterial model has (2N+3) state variables and two inputs, as defined as following:

$$x=[P_c Q_s P_1 Q_1 \ldots Q_{N-1} S_1 \ldots S_N P_d]^T : (2N+3) \times 1 \quad (30)$$

$$u=[Q_c, P_v]^T : (2\times 1) \quad (31)$$

From the continuity equation given by (16) and the constitutive law of the arterial wall given by (20), the pressures $P_i$ can be expressed in terms of the above state variables as:

$$P_i = \frac{\sqrt{\pi}\,Ee}{2S_0\sqrt{S_i}}\left(S_i + \eta\frac{dS_i}{dt} - S_0\right) \quad (32)$$

$$= \frac{\sqrt{\pi}\,Ee}{2S_0\sqrt{S_i}}\left(S_i - \frac{\eta}{\Delta z}(Q_i - Q_{i-1}) - S_0\right) \text{ for } i=1,2,\cdots,N$$

For further analysis of the nature of the hemodynamic behavior of the arterial flow, we linearized the dynamic model for local arterial segment given in (22) and (23) as follows:

$$\frac{dQ_i}{dt} + \frac{4\pi v}{S_0}Q_i - \frac{\sqrt{\pi}\,Ee\eta}{4\rho\Delta z^2\sqrt{S_0}}(Q_{i+1} - 2Q_i + Q_{i-1}) + \quad (33)$$

$$\frac{\sqrt{\pi}\,Ee}{4\rho\Delta z\sqrt{S_0}}(S_{i+1} - S_i) = 0 \text{ for } i=1,\cdots,N-1$$

$$\frac{dS_i}{dt} = -\frac{Q_i - Q_{i-1}}{\Delta z} \text{ for } i=1,2,\cdots,N \quad (34)$$

From the dynamics equation for the upstream eqs. (24)–(27), the downstream eqs. (28)–(29) and the local arterial segment eqs. (32)–(34), a state-space representation of the extended model can be described in the following format:

$$\dot{x}=Ax+Bu \quad (35)$$

where A and B are:

$$A = \begin{bmatrix} A_{up:3\times(2N+3)} \\ A_{local:(2N-1)\times(2N+3)} \\ A_{down:1\times(2N+3)} \end{bmatrix} : (2N+3)\times(2N+3) \quad (36)$$

$$B = \begin{bmatrix} \frac{1}{C_s} & 0 \\ 0 & 0 \\ \vdots & \vdots \\ 0 & 0 \\ 0 & \frac{1}{C_d R_{pd}} \end{bmatrix} : (2N+3)\times 2 \quad (37)$$

Design of Kalman Filter

Kalman filters are popularly used to estimate unknown state variables that cannot be measured directly with limited, noisy measurements of the system. To formulate a Kalman filter for the above hemodynamic system, the observation equation must be defined based on the instrumentation methods to be used. As stated previously, the objective of the Kalman filter is to continuously estimate the blood pressure merely from noninvasive and non-intrusive sensors on a peripheral skin surface. In accordance with preferred embodiments, a Kalman filter is designed based on an electrical impedance plethysmograph (EIP) and two photoplethysmographs.

A photoplethysmograph employs a pair of LED and photodetector to monitor the variation of the arterial diameter. Suppose that a photoplethysmograph is attached on the skin surface over each of the both ends of the arterial segment under consideration. Then, the two observation functions $y_1$ and $y_2$ can be simply described as a function of time by using state variables as:

$$y_1(t)=S_1(t),\ y_2(t)=S_N(t)$$

EIP uses four electrodes to measure the electrical impedance of the arterial segment surrounded by the electrodes. EIP is known to provide the absolute measurement of volumetric change of the arterial segment. Therefore, supposing that the electrodes are located at the both ends of the arterial segment under consideration, the output of EIP $y_3$ can be described in terms of the state variables as:

$$y_3(t)=V(t)=\tfrac{1}{2}S_1\Delta z+(S_2+\ldots+S_{N-1})\Delta z+\tfrac{1}{2}S_N\Delta z$$

Defining $y(t)=[y_1(t),y_2(t),y_3(t)]^T$, the observation equation can finally be defined as $$y(t)=Cx(t) \quad (38)$$

where $$C = \begin{bmatrix} 0 \cdots 0 & \overset{N+2}{1} & 0 & \cdots & \overset{N}{0} & 0 & 0 \\ 0 \cdots 0 & 0 & 0 & \cdots & 0 & 1 & 0 \\ 0 \cdots 0 & \frac{\Delta z}{2} & \Delta z & \cdots & \Delta z & \frac{\Delta z}{2} & 0 \end{bmatrix} : 3\times(2N+3)$$

Since a process noise and a measurement noise inherently exist, the state equations given in Section 2.4 must be extended as:

$$\dot{x}=Ax+Bu+Fv \quad (39)$$

$$y=Cx+w \quad (40)$$

where v and w are white noise processes, having known spectral density matrices, V and W, respectively.

Using the above equations, the state variables x(t) can be estimated by the following dynamic equations:

$$\dot{\hat{x}} = A\hat{x} + Bu + K(y - \hat{y}) \tag{41}$$

$$\hat{y} = C\hat{x} \tag{42}$$

where $\hat{y}(t)$ is the estimated measurement, $\hat{x}(t)$ is the estimated state variables, and K is the Kalman gain matrix, which is updated as:

$$K = MC^T W^{-1} \tag{43}$$

$$\dot{M} = AM + MA^T - MC^T W^{-1} CM + FVF^T \tag{44}$$

where M(t) is the covariance matrix of the state estimation error $\tilde{x}(t) = x(t) - \hat{x}(t)$. In the above derivation, we assume that v and w are uncorrelated. By updating the Kalman gain based on the nature of the process noises as described in the above equation, the Kalman filter provides the optimal estimation of the state variables. Finally, the internal blood pressures $P_i(t)$ can be estimated by substituting the estimated state variables into (32) as:

$$\hat{P}_i = \frac{\sqrt{\pi} Ee}{2S_0 \sqrt{\hat{S}_i}} \left( \hat{S}_i - \frac{\eta}{\Delta z}(\hat{Q}_i - \hat{Q}_{i-1}) - S_0 \right) \text{ for } i = 1, 2, \cdots, N \tag{45}$$

The main issue in designing the above Kalman filter is whether the system given in (39) and (40) is observable or not. If the system is not observable, a Kalman filter can not be constructed to estimate the whole state variables. As it is found in the next section, the above system is not observable. However, the observability analysis to be provided in the next section will prove that the blood pressure given in (45) can be estimated from an observable subspace of the system.

Observability Analysis

Observability Test

There are many criteria for testing the observability of a system, as described in W. S. Spector, "*Handbook of Biological Data*", Philadelphia Publisher, 1956. The standard test is the "Algebraic Controllability Theorem," as described by T. Kailath, Linear Systems, Prentice-Hall, NJ, 1980, and it simply states:

A system (A,C) of order n is observable if and only if the rank of the observability test matrix $$O = [C^T, A^T C^T, \ldots, (A^T)^{n-1} C^T] \tag{46}$$

is equal to n.

This is arguably the easiest criterion to test the observability of a system.

The above observability test was applied to the (2N+3)-th order system given by (35) and (38), and it was found that the rank of the observability matrix is 4 when N=3 or 3 when N>3, which is smaller than the order of the system. Therefore, the system is not observable and a state estimator such as a Kalman filter cannot re-construct the whole state variables. However, it will be found that the blood pressure given in (45) can be estimated from a part of the state variables and the part lies in the observable subspace of the state space. Namely, the blood pressure can be estimated from a set of the state variables which are observable with the Kalman filter designed in the previous section. To prove this argument, the whole state variables are decomposed into an observable sub-space and an unobservable sub-space.

Observable/Unobservable Sub-space Decomposition

A staircase algorithm is used for the state-space decomposition. Letting r to be the rank of the observability matrix given in (46), for the system described by (35) and (38), there exists a de-coupling similarity transformation matrix T such that $$\bar{A} = TAT^T \tag{47}$$

$$= \begin{bmatrix} A_{uo} : (2N+3-r) \times (2N+3-r) & A_{12} : (2N+3-r) \times r \\ 0 & A_o : r \times r \end{bmatrix}$$

$$\bar{C} = CT = [\, 0 \quad C_o : 3 \times r\, ]$$

Namely, the state equation can decomposed into an observable subspace and an unobservable subspace, and the r-dimensional observable subspace is represented by [$A_o$, $C_o$]. Suppose T is expressed as $$T = [T_{uo}^T : (2N+3-r) \times (2n+3) \, T_o^T : r \times (2N+3)] \tag{48}$$

Then, the transformed state variables z are decomposed into the observable state variables $z_o$ and the unobservable state variables $z_{uo}$ as:

$$z = \begin{bmatrix} z_{uo} : (2N+3-r) \times 1 \\ z_o : r \times 1 \end{bmatrix} = T^T x = \begin{bmatrix} T_{uo} \\ T_o \end{bmatrix} x \tag{49}$$

Consequently, the set of the transformed state variables $z_o = T_o x$ is observable from the output given in (38) using the Kalman filter designed in the previous section.

Blood Pressure Estimation from Observable Sub-space

The blood pressure can be calculated from state variables, according to eq. (45). This equation can be expressed in a vector form such as:

$$P_i = G_i x \tag{50}$$

where $G_i$ is a (2N+3)×1 row vector.

From the state-space analysis, it is found that there exists a r×1 row vector H such that $G = HT_o$. Therefore, the blood pressure in (50) can be described as $$P_i = G_i x = HT_o x = Hz_o \tag{51}$$

Namely, the blood pressure can be estimated from the observable variables $z_o$.

The above analysis of the state-space decomposition shows that two Photoplethysmographic sensors and one EIP sensor on an arterial segment can estimate the pressure waveforms using a Kalman filter. Based on these results, a cuff-less ambulatory blood pressure monitoring device can be designed.

Figure 7:
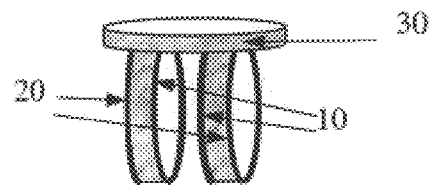
FIG. 7 shows cuff-less ambulatory pressure monitoring in accordance with an embodiment of the present invention.

FIG. 7 illustrates the sensor configuration. Photoplethysmographic sensors 10 and EIP sensors 20 are located on the two bands, which fit a human finger. The telemetry 30 can transmit signals wirelessly.

Simulation

Numerical simulations have been conducted to verify the approach. The hemodynamic process was simulated using MATLAB on a PC, and the Kalman filter for the blood pressure estimation was applied to the simulated process. The pressure estimated by the Kalman Filter was compared with the digital blood pressure measured by an arterial tonometer.

Simulation Setup

The simulation was conducted using hemodynamic parameters of a digital artery because many finger plethysmographs are commercially available and easy to be miniaturized. The following parameter values were used for the simulation:

Blood density $\rho=1.06$ gr/cm$^3$,
Blood viscosity $\mu=0.04$ poise,
Radius of digital artery r=0.5 mm,
Arterial wall viscosity $\eta=100$ dyn·s/cm$^3$,
Arterial wall elastic modulus E=7×10$^5$ N/m$^2$,
Characteristic resistance $R_{cd}=1.1\times10^4$ dyn·s/cm$^5$,
Peripheral resistance $R_{pd}=1.2\times10^5$ dyn·s/cm$^5$,
Downstream compliance $C_d=1.1\times10^{-4}$ cm$^5$/dyn,
Length of digital artery segment L=1 cm,
Nodes of the system N=3.

Figure 8:
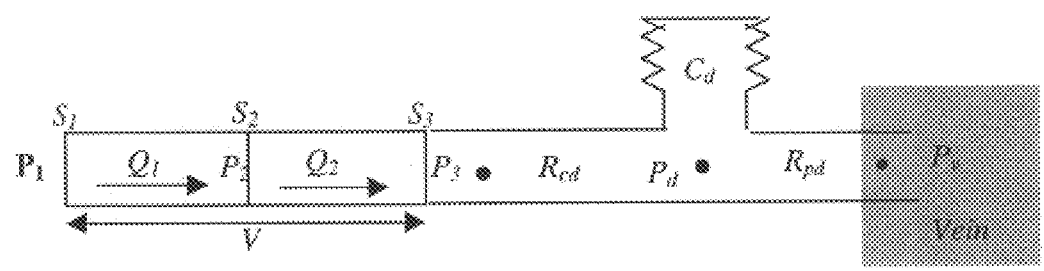
FIG. 8 shows an artery model used for simulation.

The above parameter values were obtained from published literatures such as E. Belardinelli and S. Cavalcanti, "A New Nonlinear Two-Dimensional Model of Blood Motion in Tapered and Elastic Vessels," Comut. Biol. Med., Vol. 21, pp. 1–13, 1991; W. S. Spector, "*Handbook of Biological Data*", Philadelphia Publisher, 1956; B. M. Leslie, et el., "*Digital Artery diameters: An anatomic and clinical study*", Journal of Hand Surgery, Vol. 12A, No. 5, Part 1, pp740–743, September 1987; H. Power, "*Bio-fluid Mechanics*", Computational Mechanics Publications, Boston, 1995; and K. J. Li, "*Arterial System Dynamics*", New York University Press, New York, 1987. The distributed model of a digital artery used in simulation is shown in FIG. 8. For the simplicity of the simulation, the upstream dynamic in the arterial hemodynamic model was not included. Instead, measured blood pressure signals at Section $S_1$ were used as an input to the arterial model. The definitions of the inputs, state variables and outputs in this simplified model are inputs $u=[P_1\ P_v]^T$,
state variables $x=[Q_1\ Q_2\ S_1\ S_2\ S3\ P_d]^T$,
outputs $y=[S_1\ V\ S_3]^T$.

In this setup of simulation, similarity transformation matrix T can be calculated numerically:

$$T^T = \begin{bmatrix} -0.0001 & -0.0001 & 0 & 0 & 0 & 1 \\ -0.7071 & -0.7071 & 0 & 0 & 0 & -0.0001 \\ 0.7071 & -0.7071 & 0 & 0 & 0 & 0 \\ 0 & 0 & 0 & 1 & 0 & 0 \\ 0 & 0 & 0.7071 & 0 & -0.7071 & 0 \\ 0 & 0 & -0.7071 & 0 & -0.7071 & 0 \end{bmatrix}$$

where the last four rows of T matrix represent the observable subspace $T_o$.

Figure 9:
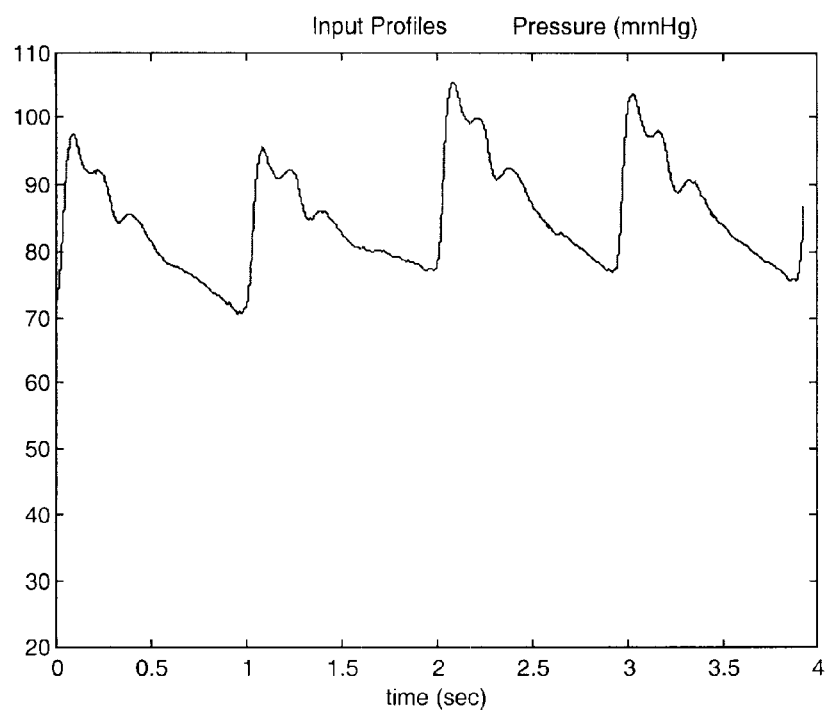
FIG. 9 shows a plot of system input: blood pressure on the boundary as a function of time.

Input $P_1$ is measured by an arterial tonometer (MILLAR, Tex.). The other input, venous pressure $P_v$ is assumed as a constant (20 mmHg). A profile of input $P_1$ is shown in FIG. 9.

Figures 10A, 10B:
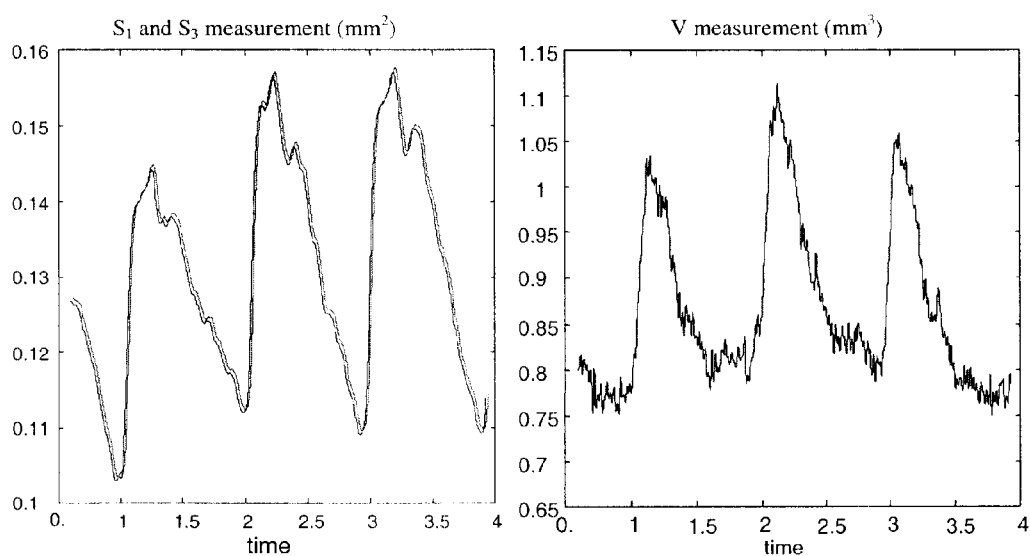
FIG. 10a shows a plot of system outputs: arterial section areas S1 and S3 as a function of time.
FIG. 10b shows a plot of system outputs: volumetric change V as a function of time.

Outputs $S_1$ and $S_3$ are measured by a pulse plethysmograph (CB Sciences, Dover, N.H.) and V is measured by an electrical impedance plethysmograph (Parks Medical Electronics, Aloha, Oreg.). The measurements are shown in FIG. 10.

Simulation Results

The Kalman filter constructed in Section 3 is simulated in MATLAB to estimate state variables and blood pressure. $P_1$, $P_v$ (u in eq. (41), depicted in FIG. 9) and measurement $Y_1$, $Y_2$, $Y_3$ (y in eq. (41), depicted in FIG. 10) are feed into a Kalman Filter. The Error covariance and Kalman filter gain are calculated for each sample of the sequence and state variables are updated according to eq. (43) and (44). Necessary state variables are then substituted into eq. (51) to estimate blood pressure.

Figure 11:
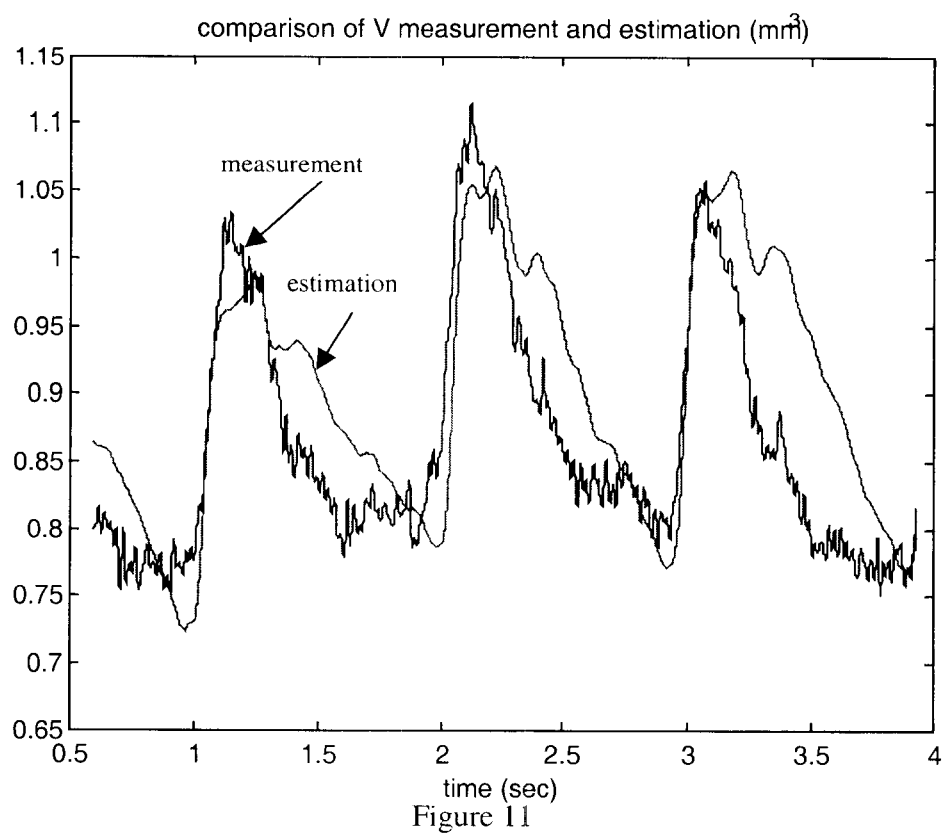
FIG. 11 shows a plot of output measurement V and estimation as a function of time.

FIG. 11 shows the comparison between the measurement and Kalman Filter estimation of the output, in which it can be seen that the Kalman Filter works very well to reduce white Gaussian noises as expected.

Figure 12:
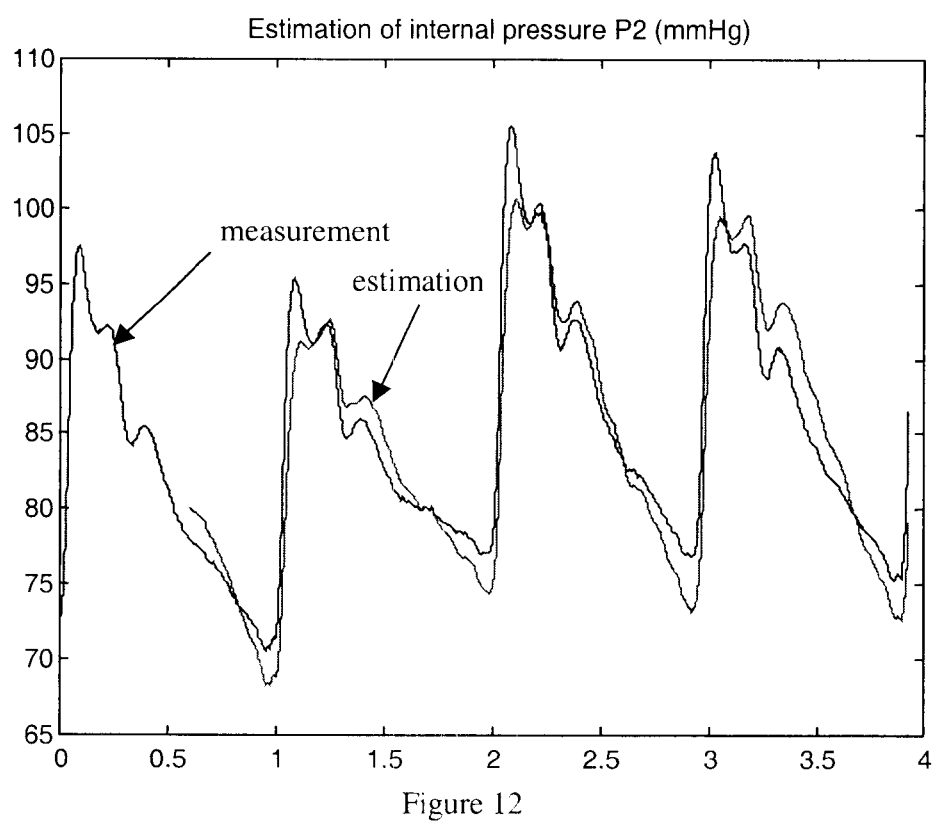
FIG. 12 shows a plot of digital blood pressure estimation by a Kalman Filter vs. measurement by an arterial tonometer as a function of time.

FIG. 12 shows the comparison between the measurement and the Kalman filter estimation of blood pressure.

From the results shown in FIG. 11 and FIG. 12, it can be concluded that a Kalman filter is very robust to noise, especially white noise. It is feasible to estimate blood pressure accurately based on the measurements from plethysmographs and a hemodynamic model.

The Monitoring System

Figure 13:
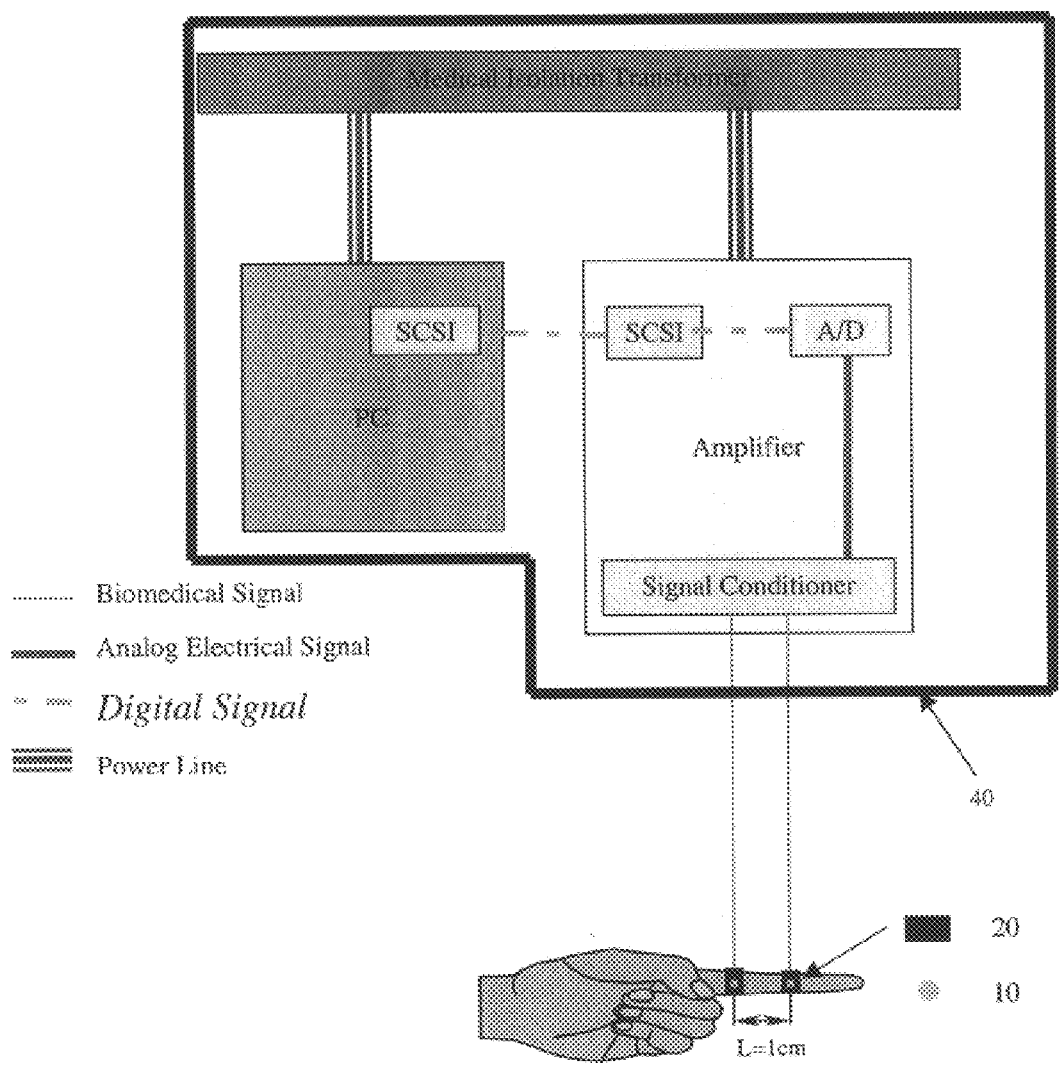
FIG. 13 shows an exemplary monitoring system.

An exemplary monitoring system is shown in FIG. 13. Outputs $S_1$ and $S_3$ are measured on the left hand middle finger by dual photo plethysmograms 10 and V is measured on the same finger by an electrical impedance plethysmogram 20. A controller 40, not necessarily consisting of any of the elements shown, derives a measure of the blood pressure. Prior to operating, the system is calibrated against a pressure cuff or other blood pressure monitoring device.

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the claims that follow.

We claim:

1. A monitoring system for monitoring a blood pressure of a patient, the monitoring system comprising:
   a. a first photoplethysmograph adapted to be placed proximate to a finger of the patient for providing a measure of change in the arterial diameter at a first location of a specified artery of the patient;
   b. a second photoplethysmograph adapted to be placed proximate to the finger of the patient and displaced relative to the first photoplethysmograph for providing a measure of change in the arterial diameter at a second location of the specified artery of the patient;
   c. an electrical impedance plethysmograph in adapted to be put in electrical contact with the finger of the patient for providing a measure of change in the electrical impedance of an arterial segment between the first and the second locations of the specified artery; and
   d. a controller deriving a measure of the blood pressure of the patient based on the measures of change in the arterial diameter at the first and second locations of the specified artery and the measure of change in the electrical impedance of an arterial segment.

2. A monitoring system according to claim 1, wherein the first photoplethysmograph is on a finger ring.

3. A monitoring system according to claim 1, wherein the first photoplethysmograph is on a first band of the finger ring and the second photoplethysmograph is on a second band of the finger ring.

4. A monitoring system according to claim 1, further including a transmitter for transmitting the measure of the blood pressure of the patient to a remote location.

5. A monitoring system for monitoring a blood pressure of a patient, the monitoring system comprising:
   a. a monitor having a first and a second band to be worn by the patient on a single finger, the monitor comprising:
      i. a first photoplethysmograph disposed on the first band for providing a first signal based on a first arterial diameter of the patient;
      ii. a second photoplethysmograph disposed on the second band for providing a second signal based on a second arterial diameter of the patient;
      iii. an electrical impedance plethysmograph disposed on the first and second bands for providing a third signal based on the electrical impedance of the a segment of an artery of the patient; and
   b. a controller for analyzing the first, second, and third signals and determining a measure of the blood pressure of the patient.

6. A method for monitoring the blood pressure of a patient, the method comprising:
   a. deriving a measure of change in the diameter of a first end of a segment of an artery of the patient;
   b. deriving a measure of change in the diameter of a second end of the segment of the artery of the patient;
   c. deriving a measure of the volume of the segment of the artery of the patient;
   d. applying a model of arterial blood flow to the derived measures of change in the diameters of the first and second ends of the arterial segment and the volume of the segment for calculating the instantaneous blood pressure of the patient.

7. A method in accordance with claim 6, wherein the step of deriving the measure of change in the diameter of the first end of a segment of an artery includes receiving a signal of a first photoplethysmograph.

8. A method in accordance with claim 6, wherein the step of deriving the measure of change in the diameter of the second end of a segment of an artery includes receiving a signal of a second photoplethysmograph.

9. A method in accordance with claim 6, wherein the step of applying a model includes applying a Kalman filter for estimating internal state variables.

* * * * *

UNITED STATES PATENT AND TRADEMARK OFFICE
CERTIFICATE OF CORRECTION

PATENT NO.    : 6,413,223 B1
DATED         : July 2, 2002
INVENTOR(S)   : Boo-Ho Yang et al.

It is certified that error appears in the above-identified patent and that said Letters Patent is hereby corrected as shown below:

Column 15,
Line 17, replace "of the a" with -- of a --.

Signed and Sealed this

Fourth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,413,223 B1
DATED : July 2, 2002
INVENTOR(S) : Boo-Ho Yang et al.

It is certified that error appears in the above-identified patent and that said Letters Patent is hereby corrected as shown below:

<u>Title page,</u>
Item [73], Assignee, replace "Massachussetts" with -- Massachusetts --.

<u>Column 14,</u>
Line 52, replace "in adapted to" with -- adapted to --.

Signed and Sealed this

Tenth Day of February, 2004

JON W. DUDAS
*Acting Director of the United States Patent and Trademark Office*